United States Patent [19]

van der Smissen

[11] Patent Number: 4,795,611
[45] Date of Patent: Jan. 3, 1989

[54] INDICATOR FOR THE DETERMINATION OF CHLORINE GAS

[75] Inventor: Carl-Ernst van der Smissen, Lübeck, Fed. Rep. of Germany

[73] Assignee: Drägerwerk AG, Fed. Rep. of Germany

[21] Appl. No.: 40,921

[22] Filed: Apr. 21, 1987

[30] Foreign Application Priority Data

Apr. 30, 1986 [DE] Fed. Rep. of Germany ....... 3614723

[51] Int. Cl.$^4$ ............................................. G01N 31/22
[52] U.S. Cl. ......................................... 422/56; 422/57; 422/86; 436/124; 436/169; 436/902
[58] Field of Search ..................... 422/56, 57, 86, 87; 436/124, 125, 169, 902

[56] References Cited

U.S. PATENT DOCUMENTS 2,942,952 6/1960 Plantz et al. ..................... 436/124

FOREIGN PATENT DOCUMENTS 1001507 7/1957 Fed. Rep. of Germany .

Primary Examiner—Barry S. Richman
Assistant Examiner—Jill Johnston
Attorney, Agent, or Firm—McGlew and Tuttle

[57] ABSTRACT

An indicator for the documentation of chlorine by discoloration of potassium iodide applied on a support is to be improved so that it is sufficiently sensitive for the documentation of the low chlorine concentrations and also has, for the documentation of high concentrations, a stable dicoloration. To this end it is provided that the indicator comprises an addition of manganese chloride.

6 Claims, 1 Drawing Sheet

U.S. Patent        Jan. 3, 1989        4,795,611
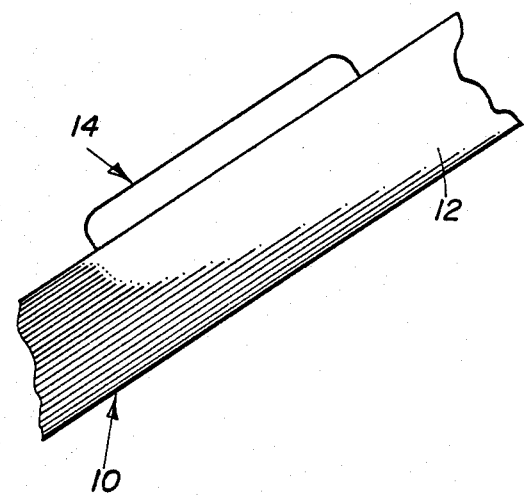

INDICATOR FOR THE DETERMINATION OF CHLORINE GAS

FIELD AND BACKGROUND OF THE INVENTION

The invention relates in general to gas indicators and in particular to a new and useful indicator for the documentation of chlorine by discoloration of potassium iodide applied on a support.

Such an indicator is described in German pat. No. 1 001 507.

The known indicator serves to detect chlorine in air. To this end, a support material, for example silica gel, is impregnated with a potassium iodide solution and filled into a test tube. When chlorine containing air flows through the test tube, free iodine is separated and colors the silica gel layer light brown. As this discoloration is not stable enough to obtain a clear indication for the determination of the chlorine content, the support is impregnated additionally with a starch solution. Now, due to the action of the released iodine on the starch, an intensive and distinct stable blue coloration of the impregnated support occurs.

With the known indicator, the fact that for stable addition of the starch on the support a further addition of zinc chloride or of mercury iodide becomes necessary is disadvantageous. This stabilization addition, however, cannot prevent the situation that, when very high chlorine concentrations are over the known impregnated support, the coloration bleaches out, thus preventing a permanent indication.

SUMMARY OF THE INVENTION

It is therefore, the object of the present invention to improve an indicator in such a way that is is sensitive enough for the documentation of low chlorine concentrations and also the resulting discoloration is durable and stable to high concentrations.

This problem is solved by an indicator which includes an addition of manganese chloride.

Accordingly it is an object of the invention to provide an improved indicator for chlorine gas which comprises a support made of silica gel or aluminum oxide and an indictor on said support of potassium iodide and manganese chloride.

A further object of the invention is to provide an indicator which has simple constituents and which is inexpensive to manufacture.

BRIEF DESCRIPTION OF THE DRAWINGS

The only FIGURE of the drawing is a schematic indication of a chlorine gas indicator constructed in accordance with the invention.

DESCRIPTION OF THE PREFERRED EMBODIMENT

Referring to the drawing in particular the invention embodied therein comprises an indicator generally designated 10 which includes a support 12 which, for example, may be of a silica gel or an aluminum oxide and with an indicator 14 on the support which comprises a potassium iodide and a manganese chloride.

The chlorine passed over the indicator oxidizes the manganese chloride to manganese dioxide, $MnO_2$, which causes a dark coloration on a support, for example of silica gel. The reaction to manganese dioxide is not influenced either by high chlorine concentrations or by prolonged storage of the indicator. If relatively low chlorine concentrations are to be detected, the formation of manganese dioxide from manganese chloride, and hence the detection sensitivity, is greatly accelerated by the presence of potassium iodide.

The reaction at the indicator in the presence of chlorine proceeds as follows:

The iodide in the potassium iodide is oxidized by the chlorine and is separated as elementary iodine. This causes a distinct browning of the originally white indicator paper. Then follows a second reaction of the indicator with the chlorine, in that under the action of the chlorine also the manganese in the manganese (II) chloride is oxidized to black manganese dioxide. This second reaction is necessary to obtain a durable discoloration of the indicator. If the indicator contains only potassium iodide, a dark coloration of the indicator is indeed achieved under chlorine action, but this dark coloration is not stable. It pales after several hours, and the indicator indication is hard to recognize, whereas the formation of manganese dioxide is irreversible.

The indicator, therefore, is especially suitable for being used as filler in test tubes for the documentation of chlorine in air. In like manner, the indicator can be applied also on a strip type support, which can be used as depletion indicator in chlorine filters.

As support material is suitable, besides the known silica gel, also aluminum oxide. As support for use of the indicator for depletion indication in chlorine filters micro glass fiber paper is suitable.

For the preparation of an indicator for the documentation of chlorine the support is impregnated with an aqueous solution of 5% potassium iodide and manganese (II) chloride each. After the impregnation, the support is dried for about 10 hours at approximately 70° C.

While a specific embodiment of the invention has been shown and described in detail to illustrate the application of the principles of the invention, it will be understood that the invention may be embodied otherwise without departing from such principles.

What is claimed is:

1. An indicator for a chlorine gas consisting essentially of a support and a colorimetric reagent of potassium iodide and manganese chloride coated on said support.

2. An indicator according to claim 1, wherein said support comprises a silica gel.

3. An indicator according to claim 1, wherein said support comprises an aluminum oxide.

4. An indicator for a chlorine gas consisting essentially of a support and a colorimetric reagent indicator of potassium iodide and manganese chloride impregnated into said support.

5. An indicator according to claim 4, wherein said support comprises a silica gel.

6. An indicator according to claim 4, wherein said support comprises an aluminum oxide.

* * * * *